United States Patent [19]

Denis et al.

[11] Patent Number: 5,312,979
[45] Date of Patent: May 17, 1994

[54] PREPARATION OF ADIPIC ACID BY HYDROCARBOXYLATION OF PENTENOIC ACIDS

[75] Inventors: Philippe Denis, Decines; Francois Metz, Vernaison; Robert Perron, Charly, all of France

[73] Assignee: Rhone-Poulenc Chimie, Courbevoie, France

[21] Appl. No.: 88,353

[22] Filed: Jul. 9, 1993

[30] Foreign Application Priority Data

Jul. 9, 1992 [FR] France .................. 92 08762

[51] Int. Cl.$^5$ ............................................. C07C 51/14
[52] U.S. Cl. ...................................................... 562/522
[58] Field of Search ........................................ 562/522

[56] References Cited

U.S. PATENT DOCUMENTS

| | | | |
|---|---|---|---|
| 3,845,121 | 10/1974 | Eubanks et al. | 260/532 |
| 3,989,747 | 11/1976 | Craddock et al. | 562/522 |
| 4,433,165 | 2/1984 | Singleton | 562/522 |
| 4,622,423 | 11/1986 | Burke | 562/522 |
| 4,788,334 | 11/1988 | Burke | 562/522 |
| 4,861,912 | 8/1989 | Drent et al. | 562/522 |

FOREIGN PATENT DOCUMENTS 2015735  4/1970  France .

*Primary Examiner*—Arthur C. Prescott
*Attorney, Agent, or Firm*—Burns, Doane, Swecker & Mathis

[57] ABSTRACT

Adipic acid is selectively prepared via hydrocarboxylation of pentenoic acids, by reacting water and carbon monoxide with at least one pentenoic acid, in the presence of a catalytically effective amount of a rhodium-based catalyst and at least one iodinated promoter therefor, at a temperature ranging from 100° to 240° C. and a pressure greater than atmospheric, and wherein (a) such reaction is carried out in the absence of a third reaction solvent and (b) the carbon monoxide partial pressure, measured at 25° C., is less than or equal to 20 bar.

8 Claims, No Drawings

PREPARATION OF ADIPIC ACID BY HYDROCARBOXYLATION OF PENTENOIC ACIDS

BACKGROUND OF THE INVENTION

1. Field of the Invention

The present invention relates to the preparation of adipic acid by hydrocarboxylation of pentenoic acids, and, more especially, by reacting water and carbon monoxide with at least one pentenoic acid, in the presence of a rhodium-based catalyst, as well as at least one iodinated promoter therefor.

2. Description of the Prior Art

Published European Patent Application No. 188,209 describes a process for preparing linear dicarboxylic acids, in particular adipic acid, by reaction of unsaturated monocarboxylic acids, in particular penten-3-oic acid, carbon monoxide and water, in the presence of a rhodium-based catalyst and of an iodinated promoter, the reaction being carried out in a solvent such as methylene chloride at a temperature of 100° to 240° C. and under a total pressure of between 14 and 240 atm; a temperature of between 150° and 180° C. and a total pressure of between 24 and 40 atmospheres are indicated as preferable. The carbon monoxide partial pressure is generally between 10 and 35 atmospheres and preferably between 10 and 17 atmospheres. The selection of the solvent is considered to be critical for the process described and it is even indicated that solvents such as acetic acid are undesirable due to the low degrees of linearity obtained in their presence.

Likewise, it is maintained that nonpolar solvents such as cyclohexane and toluene are also undesirable, due to their propensity to directly promote the formation of branched compounds and, indirectly, saturated monocarboxylic acids.

Published European Patent Application No. 0,274,076 describes a process for preparing linear carboxylic acids by hydroxycarboxylation of unsaturated esters or of terminally unsaturated alkenes comprising from 4 to 16 carbon atoms, in the presence of a rhodium-based catalyst and of an iodinated promoter. The reaction is carried out in a solvent indiscriminately selected from among methylene chloride, 1,2-dichloroethane and aromatic solvents. An aliphatic or aromatic acid having a $pK_a$ of between 4.2 and 5.2 is present as the reaction accelerator. The carbon monoxide partial pressure is between 10 and 200 atmospheres and preferably between 13 and 20 atmospheres.

However, when using pentenoic ester starting materials, the formation of methyl monoadipate is essentially observed.

EP-A-0,477,112 describes the preparation of adipic acid by hydrocarboxylation of pentenoic acids in the presence of rhodium and of an iodinated promoter in a solvent selected from among the carboxylic acids.

In sum, all of the processes of the prior art are carried out in a solvent of one type or another.

SUMMARY OF THE INVENTION

Accordingly, a major object of the present invention is the provision of an improved process for selectively preparing adipic acid by hydrocarboxylation of pentenoic acids in the presence of a rhodium-based catalyst and of an iodinated promoter, but in the absence of a third solvent, namely, exclusively employing one or more pentenoic acids.

Briefly, the present invention features a process for preparing adipic acid by reacting water and carbon monoxide with at least one pentenoic acid, in the presence of a catalytically effective amount of a rhodium-based catalyst and of at least one iodinated promoter therefor, at a temperature ranging from 100° to 240° C., at a pressure greater than atmospheric pressure, with the proviso that (a) the reaction is carried out in the absence of a third solvent, and (b) the carbon monoxide partial pressure, measured at 25° C., is less than or equal to 20 bar.

DETAILED DESCRIPTION OF PREFERRED EMBODIMENTS OF THE INVENTION

More particularly according to the present invention, by "pentenoic acid" are intended penten-2-oic acid, penten-3-oic acid, penten-4-oic acid, and/or mixtures thereof.

Penten-4-oic acid provides good results, but is still not readily available.

Penten-3-oic acid, whether used alone or in admixture with its isomers, is more particularly suitable, considering its accessibility and the satisfactory results which it provides within the scope of the present invention.

The pentenoic acid starting materials may, of course, contain minor amounts of byproducts formed during their preparation, such as, for example, valeric acid, methylbutyrolactones, adipic acid, methylglutaric acid and ethylsuccinic acid.

The process according to this invention requires the presence of a rhodium-based catalyst. Any rhodium source may be used.

Exemplary rhodium sources suitable for the process of the invention include:

Rh metal, $Rh_2O_3$
$RhCl_3$, $RhCl_3.3H_2O$,
$RhBr_3$, $RhBr_3.3H_2O$,
$RhI_3$, $Rh(NO_3)_3$, $Rh(NO_3)_3.2H_2O$,
$Rh_2(CO)_4Cl_2$, $Rh_2(CO)_4Br_2$, $Rh_2(CO)_4I_2$,
$Rh(CO)Cl[P(C_6H_5)_3]_2$,
$Rh[P(C_6H_5)_3]_2(CO)I$,
$Rh[P(C_6H_5)_3]_3Br$,
$Rh_4(CO)_{12}$, $Rh_6(CO)_{16}$, $Rh(CO)_2(acac)$,
$Rh(Cod)(acac)_2$, $Rh(acac)_3$,
$Rh_2(Cod)_2Cl_2$, $Rh_2(cO_2Ch_{34}$,
$HRh(CO) [P(C_6H_5)_3]_3$,
(Cod = 1,5-cyclooctadiene, acac = acetylacetonate).

More particularly preferred are:
$HRh(CO)[P(C_6H_5)_3]_3$,
$Rh(CO)Cl[P(C_6H_5)_3]_2$,
$Rh_2(Cod)_2Cl_2$,
$Rh_2(CO)_4Cl_2$,
$RhI_3$, $RhCl_3.3H_2O$, $Rh(acac)_3$,
$Rh(Cod)(acac)_2$, $Rh_2(CO_2CH_3)_4$, $Rh_4(CO)_{12}$, and $Rh_5(CO)_{16}$.

The amount of rhodium to be used can vary over wide limits.

In general, an amount, expressed in mole of metallic rhodium per liter of reaction mixture, ranging to $10^{-4}$ to $10^{-1}$ provides satisfactory results. Lesser amounts can be used; however, the reaction velocity is then observed to be low. Greater amounts present disadvantages only from an economic standpoint.

Preferably, the concentration of rhodium ranges from $5 \cdot 10^{-4}$ to $10^{-2}$, inclusive, mol/l.

By "iodinated promoter" are intended HI and the organoiodine compounds that generate HI under the reaction conditions and, in particular, the $C_1$-$C_{10}$ alkyl iodides, with methyl iodide being more particularly preferred.

The amount of iodinated promoter to be used is, in general, such that the I/Rh molar ratio is greater than or equal to 0.1. It is not desirable for this ratio to exceed 20. Preferably, the I/Rh molar ratio ranges from 1 to 4 inclusive.

The presence of water is critical to carry out the process according to the present invention. In general, the amount of water used is such that the water/pentenic acid(s) molar ratio ranges from 0.01 to 10, inclusive.

A lesser amount presents the disadvantage of excessively limiting the conversion. A greater amount is not desirable because of the resulting loss in catalytic activity.

In an essential characteristic of the subject process, the carbon monoxide partial pressure, measured at 25° C., is less than or equal to 20 bar.

When the carbon monoxide partial pressure, measured at 25° C., is greater than this value, the selectivity in respect of linear and/or branched diacids is very low and the formation of significant amounts of 4-methylbutyrolactone, an undesirable compound, is observed.

A minimum carbon monoxide partial pressure of 0.5 bar (measured at 25° C.) is advantageous.

Preferably, the carbon monoxide partial pressure, measured at 25° C., is less than or equal to 10 bar.

It is possible to use carbon monoxide which is substantially pure or of technical grade, such as is commercially available.

As indicated above, the reaction temperature advantageously ranges from 100° C. to 240° C. For good results, the reaction temperature ranges from 160° to 190° C., inclusive.

The reaction is carried out at a pressure greater than atmospheric pressure, and, generally, in the liquid phase.

The total pressure can vary over certain limits which will depend on the procedure employed, on the carbon monoxide partial pressure and on those of the constituents of the reaction mixture at the reaction temperature selected, and, if appropriate, on the autogenous pressure of the pentenoic acid(s) present.

The reaction mixture contains water, one or more rhodium sources, one or more iodinated promoters and, if appropriate, all or a fraction of the pentenoic acid(s) involved, and reaction products.

Upon completion of the reaction or at the end of the time allotted thereto, adipic acid is separated by any suitable means, for example by crystallization.

In order to further illustrate the present invention and the advantages thereof, the following specific examples are given, it being understood that same are intended only as illustrative and in nowise limitative.

EXAMPLE 1

The following materials were introduced into a glass flask purged beforehand with argon:
(i) 1.31 mmol of rhodium in the form of [RhCl(Cod)]$_2$;
(ii) 0.35 g (2.5 mmol) of CH$_3$I;
(iii) 2.29 g (127 mmol) of water;
(iv) 55.2 g (552 mmol) of penten-3-oic acid.

The flask was placed in a 125-ml autoclave.

The autoclave was hermetically closed, placed into an oven equipped with agitation and connected to a supply of pressurized gas. 2 bar of CO were admitted while cold and the mixture was heated to 175° C. over 20 minutes. When this temperature was attained, the pressure was adjusted to 8 bar.

After a period of reaction of 90 minutes, CO absorption had ceased; the autoclave was then cooled and degassed.

The reaction solution was analyzed by gas phase chromatography and by high pressure liquid chromatography.

The amounts of products formed (molar yield in relation to penten-3-oic acid transformed) were as follows:

| Compound | Structure | Yield |
|---|---|---|
| Valeric acid (Pa): | ~~COOH | = 0% |
| Penten-4-oic acid: (P4): | CH$_2$=CH-CH$_2$-CH$_2$-COOH | = 9.5% |
| Penten-2-oic acid (P2): | CH$_3$-CH$_2$-CH=CH-COOH | = 7.5% |
| 4-Methylbutyrolactone (M4L): | (γ-valerolactone ring) | = 16% |
| Ethylsuccinic acid (A3): | HOOC-CH(C$_2$H$_5$)-CH$_2$-COOH | = 0% |
| Methylglutaric acid (A2): | HOOC-CH(CH$_3$)-CH$_2$-CH$_2$-COOH | = 16% |
| Adipic acid (A1): | HOOC-(CH$_2$)$_4$-COOH | = 57% |

The degree of linearity (L) was 77%. The degree of conversion of penten-3-oic acid (DC) was 47%.

The productivity, expressed in grams of adipic acid produced per hour and per liter of reaction mixture (calculated over 30 min of CO absorption), was 1,100 g/h.l.

COMPARATIVE EXAMPLE 1(a)

The procedure of Example 1 was repeated under the same conditions, but using the following charges:
(i) 1.31 mmol of rhodium in the form of [RhCl(Cod)]$_2$;
(ii) 0.35 g (2.5 mmol) of CH$_3$I;
(iii) 2.29 g (127 mmol) of water;
(iv) 4.88 g (48.8 mmol) of penten-3-oic acid;
(v) 43.2 g of acetic acid.

The following results were obtained:
(a) DC of P3: 100%
(b) Degree of linearity: 73%
(c) Yield of adipic acid: 62%
(d) Productivity: 130 g/h.l

EXAMPLE 2

The procedure of Example 1 was repeated, under the following conditions:
Temperature: 175° C.;
CO pressure: 20 bar;

Duration of temperature: 180 min; and employing the following charges:

(i) 0.192 mmol of rhodium in the form of [RhCl(Cod)]$_2$; p1 (ii) 0.105 g (0.468 mmol) of HI in the form of a 57% solution in water; [RhCl(Cod)]$_2$;

(ii) 0.105 g (0.468 mmol) of HI in the form of a 57% solution in water;

(iii) 2.31 g (128 mmol) of water;

(iv) 53.63 g (536 mmol) of penten-3-oic acid.

The following results were obtained:

(a) DC of P3: 41%

(b) Degree of linearity: 55%

(c) Yield of adipic acid: 42%

(d) Productivity: 170 g/h.l

EXAMPLE 3

The procedure of Example 1 was repeated, under the following conditions:

Temperature: 175° C.;

CO pressure: 8 bar;

Duration of temperature: 205 min; and employing the following charges:

(i) 0.192 mmol of rhodium in the form of [RhCl(Cod)]$_2$;

(ii) 0.105 g (0.468 mmol) of HI in the form of a 57% solution in water;

(iii) 2.31 g (128 mmol) of water;

(iv) 53.76 g (538 mmol) of penten-3-oic acid.

The following results were obtained:

(a) DC of P3: 38%;

(b) Degree of linearity: 63%

(c) Yield of adipic acid: 49%

(d) Productivity: 150 g/h.l

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of adipic acid, comprising reacting water and carbon monoxide with at least one pentenoic acid, in the presence of a catalytically effective amount of a rhodium-based catalyst and at least one iodinated promoter therefor, at a temperature ranging from 100° to 240° C. and at a pressure greater than atmospheric, with the proviso that (a) said reaction is carried out in the absence of a third reaction solvent and (b) the carbon monoxide partial pressure, measured at 25° C., is less than or equal to 20 bar.

2. The process as defined in claim 1, wherein the rhodium concentration in the reaction mixture ranges from $10^{-4}$ to $10^{-1}$ mol/l.

3. The process as defined by claim 1, wherein the I/Rh molar ratio is greater than or equal to 0.1.

4. The process as defined by claim 3, wherein the I/Rh molar ratio is less than or equal to 20.

5. The process as defined by claim 1, wherein the water/pentenoic acid(s) molar ratio ranges from 0.01 to 10.

6. The process as defined by claim 1, carried out at a temperature ranging from 160° to 190° C.

7. The process as defined by claim 1, wherein the carbon monoxide partial pressure, measured at 25° C., is less than or equal to 10 bar.

8. The process as defined by claim 1, said at least one pentenoic acid comprising penten-3-oic acid, or admixture thereof with penten-4-oic acid and/or penten-2-oic acid.

* * * * *